United States Patent
Lo

(10) Patent No.: US 10,037,442 B2
(45) Date of Patent: Jul. 31, 2018

(54) ANTI-COPY ELECTRONIC DEVICE

(71) Applicant: Szu Chi Lo, Nantou (TW)

(72) Inventor: Szu Chi Lo, Nantou (TW)

(*) Notice: Subject to any disclaimer, the term of this patent is extended or adjusted under 35 U.S.C. 154(b) by 216 days.

(21) Appl. No.: 15/202,780

(22) Filed: Jul. 6, 2016

(65) Prior Publication Data

US 2018/0012044 A1    Jan. 11, 2018

(51) Int. Cl.
| | |
|---|---|
| G06F 21/00 | (2013.01) |
| G06F 21/88 | (2013.01) |
| H04W 4/00 | (2018.01) |
| G01J 1/42 | (2006.01) |
| G01J 5/60 | (2006.01) |
| G01N 33/00 | (2006.01) |
| G06F 21/71 | (2013.01) |
| G06F 21/86 | (2013.01) |
| H04W 4/70 | (2018.01) |

(52) U.S. Cl.
CPC .............. *G06F 21/88* (2013.01); *G01J 1/429* (2013.01); *G01J 5/60* (2013.01); *G01N 33/0036* (2013.01); *G06F 21/71* (2013.01); *G06F 21/86* (2013.01); *H04W 4/005* (2013.01); *H04W 4/70* (2018.02)

(58) Field of Classification Search
None
See application file for complete search history.

(56) References Cited

U.S. PATENT DOCUMENTS

| | | | | |
|---|---|---|---|---|
| 5,945,915 A | * | 8/1999 | Cromer | G06F 1/181 340/568.1 |
| 9,143,741 B1 | * | 9/2015 | Fu | H04N 7/18 |
| 9,820,315 B2 | * | 11/2017 | Le Guen | H04W 4/70 |
| 2007/0056043 A1 | * | 3/2007 | Onyon | G06F 21/88 726/26 |
| 2010/0046553 A1 | * | 2/2010 | Daigle | G06F 21/35 370/474 |
| 2011/0122858 A1 | * | 5/2011 | Yashiro | H04W 64/00 370/338 |

(Continued)

OTHER PUBLICATIONS

Krekan, Jan; Pleva, Matus; Dobos, Lubomir. Statistical Models Based Password Candidates Generation for Specified Language Used in Wireless LAN Security Audit. 2013 20th International Conference on Systems, Signals and Image Processing (IWSSIP). http://ieeexplore.ieee.org/stamp/stamp.jsp?tp=&arnumber=6623458.*

(Continued)

*Primary Examiner* — Jeremiah Avery

(74) *Attorney, Agent, or Firm* — Muncy, Geissler, Olds & Lowe, P.C.

(57) ABSTRACT

An anti-copy electronic device contains: a wireless signal controller having a sensor, and the wireless signal controller and the sensor are accommodated in a casing. The sensor has humidity detection, pressure detection, lights detection, color temperature detection, ultraviolet (UV) detection, and special gases detection in an interior space of the casing. After the casing is removed, the sensor detects a change of humidity, pressure, lights, color temperature, ultraviolet (UV), and special gases in the interior space and sends an indication signal to the wireless signal controller so that the wireless signal controller destroys a password setting program of the wireless signal controller, thus avoiding copy of the password setting program.

6 Claims, 1 Drawing Sheet

(56) References Cited

U.S. PATENT DOCUMENTS

| | | | | |
|---|---|---|---|---|
| 2013/0091564 A1* | 4/2013 | Fitzgerald | ............... | G06F 21/88 |
| | | | | 726/17 |
| 2013/0237272 A1* | 9/2013 | Prasad | ................. | H04B 7/0617 |
| | | | | 455/517 |
| 2014/0128032 A1* | 5/2014 | Muthukumar | ........... | H01Q 3/00 |
| | | | | 455/411 |
| 2014/0364099 A1* | 12/2014 | Pai | .......................... | H04L 63/08 |
| | | | | 455/418 |
| 2014/0373184 A1* | 12/2014 | Mahaffey | ................ | G06F 21/88 |
| | | | | 726/35 |
| 2015/0242644 A1* | 8/2015 | Sonasath | ................. | G06F 21/88 |
| | | | | 726/26 |
| 2016/0234186 A1* | 8/2016 | Leblond | ................. | G06Q 10/06 |

OTHER PUBLICATIONS

Mishra, Brojo Kishore; Sahu, Minakshi; Das, Satya Naryan. Intusion Detection Systems for High Performance Computing Environment. 2014 International Conference on High Performance Computing and Applications (ICHPCA). http://ieeexplore.ieee.org/stamp/stamp.jsp?tp=&arnumber=7045369.*

* cited by examiner

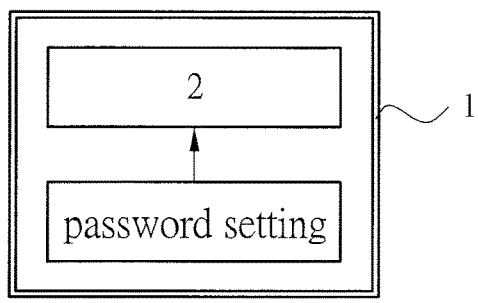
PRIOR ART  FIG.1
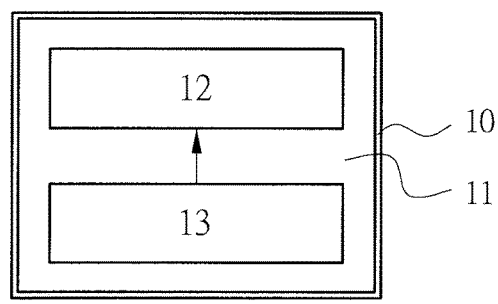
FIG.2
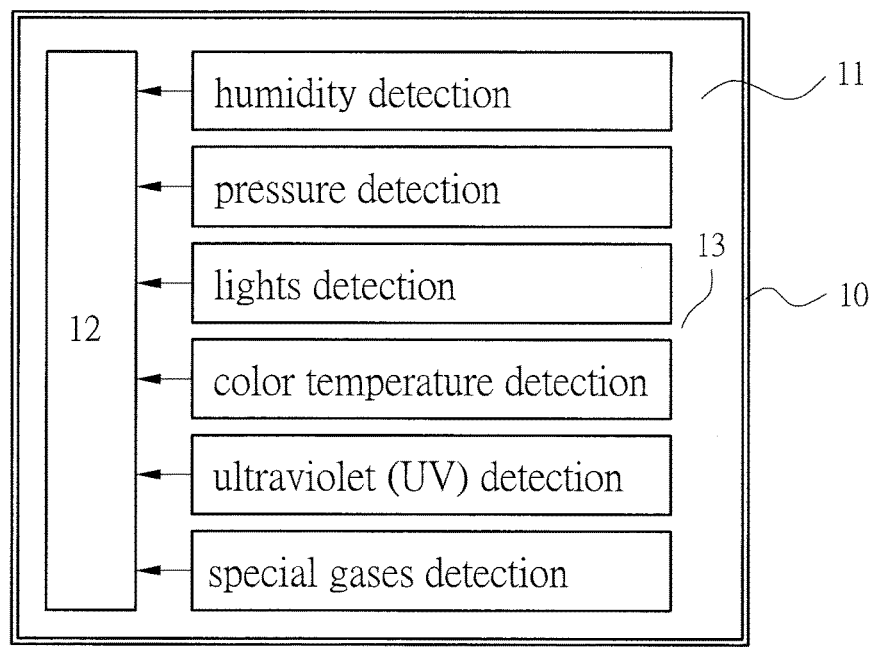
FIG.3

ANTI-COPY ELECTRONIC DEVICE

FIELD OF THE INVENTION

The present invention relates to an anti-copy electronic device which detects a change in a casing of the anti-copy electronic device so as to destroy a password setting program of the wireless signal controller, thus avoiding copy of the password setting program.

BACKGROUND OF THE INVENTION

Referring to FIG. 1, a conventional electronic device contains a casing 1 in which a wireless signal controller 2 is accommodated, and the wireless signal controller 2 has password setting so as to set password, however, the password setting is copied easily.

The present invention has arisen to mitigate and/or obviate the afore-described disadvantages.

SUMMARY OF THE INVENTION

The primary objective of the present invention is to provide an anti-copy electronic device which detects a change in a casing of the anti-copy electronic device so as to destroy a password setting program of the wireless signal controller, thus avoiding copy of the password setting program.

To obtain above-mentioned objective, an anti-copy electronic device provided by the present invention contains: a wireless signal controller having a sensor, and the wireless signal controller and the sensor are accommodated in a casing.

The sensor has humidity detection so as to detect humidity in an interior space of the casing.

After the casing is removed, the sensor detects a change of the humidity in the interior space and sends an indication signal to the wireless signal controller so that the wireless signal controller destroys a password setting program of the wireless signal controller, thus avoiding copy of the password setting program.

Preferably, the sensor has pressure detection so as to detect pressure in the interior space of the casing, and wherein after the casing is removed, the sensor detects a change of the pressure in the interior space and sends the indication signal to the wireless signal controller so that the wireless signal controller destroys the password setting program of the wireless signal controller, thus avoiding the copy of the password setting program.

Preferably, the sensor has lights detection so as to detect lights in the interior space of the casing, and wherein after the casing is removed, the sensor detects a change of the lights in the interior space and sends the indication signal to the wireless signal controller so that the wireless signal controller destroys the password setting program of the wireless signal controller, thus avoiding the copy of the password setting program.

Preferably, the sensor has color temperature detection so as to detect color temperature in the interior space of the casing, and wherein after the casing is removed, the sensor detects a change of the color temperature in the interior space and sends the indication signal to the wireless signal controller so that the wireless signal controller destroys the password setting program of the wireless signal controller, thus avoiding the copy of the password setting program.

Preferably, the sensor has ultraviolet (UV) detection so as to detect ultraviolet (UV) in the interior space of the casing, and wherein after the casing is removed, the sensor detects a change of the ultraviolet (UV) in the interior space and sends the indication signal to the wireless signal controller so that the wireless signal controller destroys the password setting program of the wireless signal controller, thus avoiding the copy of the password setting program.

Preferably, the sensor has special gases detection so as to detect special gases in the interior space of the casing, and wherein after the casing is removed, the sensor detects a change of the special gases in the interior space and sends the indication signal to the wireless signal controller so that the wireless signal controller destroys the password setting program of the wireless signal controller, thus avoiding the copy of the password setting program.

BRIEF DESCRIPTION OF THE DRAWINGS

FIG. 1 is a block diagram showing a controlling method of a sensor of a conventional electronic device.

FIG. 2 is a block diagram showing the configuration of an anti-copy electronic device according to a preferred embodiment of the present invention.

FIG. 3 is a block diagram showing a controlling method of the anti-copy electronic device according to the preferred embodiment of the present invention.

DETAILED DESCRIPTION OF THE PREFERRED EMBODIMENTS

With reference to FIGS. 2 and 3, an anti-copy electronic device according to a preferred embodiment of the present invention comprises: a wireless signal controller 12 having a sensor 13, and the wireless signal controller 12 and the sensor 13 are accommodated in a casing 10, wherein the sensor 13 has humidity detection, pressure detection, lights detection, color temperature detection, ultraviolet (UV) detection, and special gases detection so as to detect humidity, pressure, lights, color temperature, ultraviolet (UV), and special gases in an interior space 11 of the casing 10.

Preferably, when the casing 10 is closed completely, it is dark in the interior space 11 of the casing 10, and the humidity, the pressure, the lights, the color temperature, the ultraviolet (UV), and the special gases in the interior space 11 are different from those outside the casing 10.

As desiring to copy a password setting program of the wireless signal controller 12, the casing 10 is removed, and the humidity, the pressure, the lights, the color temperature, the ultraviolet (UV), and the special gases (such as carbon dioxide, nitrogen, and ozone) in the interior space 11 change, hence the sensor 13 detects a change of the humidity, the pressure, the lights, the color temperature, the ultraviolet (UV), and the special gases in the interior space 11 and sends an indication signal to the wireless signal controller 12 so that the wireless signal controller 12 destroys the password setting program of the wireless signal controller 12, thus avoiding copy of the password setting program.

Because the casing 10 is closed completely, at least one battery (not shown) is housed in the casing 10 and its electricity is chargeable. For example, the at least one battery charges its electricity in electromagnetic charging manner, i.e., an electromagnetic coil (not shown) is arranged in the casing 10 so as to sense electromagnetism and produce electricity.

Preferably, a method of avoiding copying a password setting program of the wireless signal controller 12 of the anti-copy electronic device contains steps of:

1. Providing the wireless signal controller 12 in the anti-copy electronic device, wherein the wireless signal controller 12 has the sensor 13 and is accommodated in the casing 10;

2. Detecting a change of the humidity, the pressure, the lights, the color temperature, the ultraviolet (UV), and the special gases in the interior space 11 of the casing 10 by using the sensor 13, after removing the casing 10; and 3. Sending the indication signal to the wireless signal controller 12 from the sensor 13 so that the wireless signal controller 12 destroys the password setting program of the wireless signal controller 12, thus avoiding copy of the password setting program.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. An anti-copy electronic device comprising: a wireless signal controller having a sensor, and the wireless signal controller and the sensor being accommodated in a casing;
   wherein the sensor has humidity detection so as to detect humidity in an interior space of the casing; and
   wherein after the casing is removed, the sensor detects a change of the humidity in the interior space and sends an indication signal to the wireless signal controller so that the wireless signal controller destroys a password setting program of the wireless signal controller, thus avoiding copy of the password setting program.

2. The anti-copy electronic device as claimed in claim 1, wherein the sensor has pressure detection so as to detect pressure in the interior space of the casing, and wherein after the casing is removed, the sensor detects a change of the pressure in the interior space and sends the indication signal to the wireless signal controller so that the wireless signal controller destroys the password setting program of the wireless signal controller, thus avoiding the copy of the password setting program.

3. The anti-copy electronic device as claimed in claim 1, wherein the sensor has lights detection so as to detect lights in the interior space of the casing, and wherein after the casing is removed, the sensor detects a change of the lights in the interior space and sends the indication signal to the wireless signal controller so that the wireless signal controller destroys the password setting program of the wireless signal controller, thus avoiding the copy of the password setting program.

4. The anti-copy electronic device as claimed in claim 1, wherein the sensor has color temperature detection so as to detect color temperature in the interior space of the casing, and wherein after the casing is removed, the sensor detects a change of the color temperature in the interior space and sends the indication signal to the wireless signal controller so that the wireless signal controller destroys the password setting program of the wireless signal controller, thus avoiding the copy of the password setting program.

5. The anti-copy electronic device as claimed in claim 1, wherein the sensor has ultraviolet (UV) detection so as to detect ultraviolet (UV) in the interior space of the casing, and wherein after the casing is removed, the sensor detects a change of the ultraviolet (UV) in the interior space and sends the indication signal to the wireless signal controller so that the wireless signal controller destroys the password setting program of the wireless signal controller, thus avoiding the copy of the password setting program.

6. The anti-copy electronic device as claimed in claim 1, wherein the sensor has special gases detection so as to detect special gases in the interior space of the casing, and wherein after the casing is removed, the sensor detects a change of the special gases in the interior space and sends the indication signal to the wireless signal controller so that the wireless signal controller destroys the password setting program of the wireless signal controller, thus avoiding the copy of the password setting program.

\* \* \* \* \*